US006391941B1

(12) United States Patent
Williams

(10) Patent No.: US 6,391,941 B1
(45) Date of Patent: May 21, 2002

(54) ANTIMICROBIAL THERAPEUTIC PUTTY

(75) Inventor: Colin David Williams, Signal Mountain, TN (US)

(73) Assignee: Magister Corporation, Chattanooga, TN (US)

( * ) Notice: Subject to any disclaimer, the term of this patent is extended or adjusted under 35 U.S.C. 154(b) by 0 days.

(21) Appl. No.: 09/472,298

(22) Filed: Dec. 27, 1999

Related U.S. Application Data

(60) Provisional application No. 60/114,345, filed on Dec. 29, 1998.

(51) Int. Cl.[7] .................................................. C08K 5/06
(52) U.S. Cl. ....................................................... 523/122
(58) Field of Search ......................................... 523/122

(56) References Cited

U.S. PATENT DOCUMENTS

| | | |
|---|---|---|
| 2,541,851 A | 2/1951 | Wright |
| 3,506,720 A | 4/1970 | Basel et al. |
| 3,629,477 A | 12/1971 | Basel et al. |
| 3,677,997 A * | 7/1972 | Kaiser .................. 260/332 |
| 4,568,536 A | 2/1986 | Kronenthal et al. |
| 4,956,404 A * | 9/1990 | Pelzig .................... 524/48 |
| 5,310,421 A | 5/1994 | Reyes et al. |
| 5,319,021 A | 6/1994 | Christy |
| 5,446,075 A | 8/1995 | Gibbon |
| 5,607,993 A | 3/1997 | Christy |

OTHER PUBLICATIONS

Ciba Specialty Chemicals Corporation; Material Safety Data Sheet; IRGASAN DP 300, Nov. 06, 1998; 6 pages; MSDS No. 235; Ciba Specialty Chemicals Corporation, Consumer Care, P.O. Box 2444, High Point, NC 27261–2444.

Ciba Specialty Corporation; IRGASAN® DP 300, Broad Spectrum Antimicrobial Agent, Aug., 1998, 1 page.

Ciba Specialty Chemicals Corporation; IRGASAN® DP 300, IRGACARE®MP, IRGACIDE LP® 10, Antimicrobials, General Information on Chemical, Physical and Microbiological Properties; Title Page, Table of Content page, pp. 3–14 (16 pages total).

* cited by examiner

Primary Examiner—Paul R. Michl
(74) Attorney, Agent, or Firm—Alston & Bird LLP

(57) ABSTRACT

An antimicrobial therapeutic putty remains substantially free of undesirable living contaminants, such as bacteria, fungi, viruses, and the like, that come into contact with the putty through normal use of the putty. The putty is a kneadable putty that includes a borosiloxane compound which exhibits sufficient resistance and elasticity to render it suitable for hand exercise, and the borosiloxane compound includes an antimicrobial agent in a concentration sufficient to render the compound antimicrobial without adversely affecting the physical properties of the compound.

5 Claims, No Drawings

ANTIMICROBIAL THERAPEUTIC PUTTY

CROSS-REFERENCE TO RELATED APPLICATION

This application claims the benefit of copending U.S. Provisional Patent Application No. 60/114,345, filed on Dec. 29, 1998, which is incorporated herein by reference.

FIELD OF THE INVENTION

The invention generally relates to putty for use in physical therapy and/or play. More specifically, the invention relates to kneadable putties, and in particular therapeutic putties, which resist the acceptance and propagation of undesirable contaminants.

BACKGROUND OF THE INVENTION

Kneadable putties such as those made from borosiloxane are commonly used in physical and occupational therapy to strengthen a patient's muscle control and strength and to restore performance of a patient's hands, fingers and/ or arms. A borosiloxane bouncing putty has also long been commercially available for use as a toy under the trademark "Silly Putty®". Such putties have the ability to be kneaded and stretched, and can be provided in a variety of different resistances. Examples of borosiloxane putties are shown, for example, in U.S. Pat. No. 2,541,851 to Wright, U.S. Pat. No. 3,677,997 to Kaiser et al, U.S. Pat. No. 5,319,021 to Christie, and U.S. Pat. No. 5,446,075 to Gibbon.

There are a variety of putties commercially available including those having different colors, varied resistance levels, those having varied levels of "oily feel", those having chips which can be added to the putty to increase the resistance thereof, those which are microwaveable to provide warmth to the joints and muscles during the exercise process, those which arc uncolored, and the like. Other types commercially available include those having stretch memory so that the more you stretch them, the more they resist the force, those which resist breaking, those which have a tendency to retain their initial shape, those which resist cold flow, and those which resist sticking to the skin and hands and to items such as carpet. Other qualities generally deemed to be desirable in therapeutic putties include colorfastness and resistance to color bleeding, as well as an ability to retain the kneadability over an extended period of time.

The type of putty used in physical and occupational therapy is generally selected by the therapist to provide the physical characteristics desired to achieve optimal performance by the patient during therapy sessions. The putties are used by the therapists to assist in increasing patient strength, endurance and mobility, to increase the range of motion of a wearer's fingers, hand or arm, to encourage proper tendon motion and hand closure and opening, and the like.

When used for hand exercise and therapy, the lumps of therapy putty are handled and kneaded by both the patient and the therapist. Through contact with the skin of these individuals, the putty can pick up contaminants such as bacteria, fungi, viruses, and the like. In addition, when the putty comes in contact with other things such as the surface of a table, it can also pick up unwanted contaminants. Such bacteria, fungal spores and other material are thus picked up and retained by the putty, where they are kneaded into the material through subsequent use of the putty material by the patient and the therapists As a result, such contaminants become part of the putty where they can remain and even propagate, and in turn be passed to a putty user during subsequent uses. Furthermore, putty materials are often used by more than one patient. Therefore, the contaminants picked up by the putty during use by one patient can be transferred onto the next patient and/or therapist. This can represent a significant problem, particularly when the putty is to be used by patients or therapists having decreased levels of immunities such as those who are ill or recovering from injuries. Furthermore, because such putties are often used in hospital or clinic environments where germs may be more rampant, the opportunity for their transmission can be even greater.

To date, no efficient and cost-effective means for sterilizing the putty following use has been available. Therefore, heretofore therapeutic putties have routinely been re-used throughout a number of therapy sessions, without regard to the spread of disease and germs, which is disadvantageous.

SUMMARY OF THE INVENTION

The present invention is a kneadable putty that includes an antimicrobial agent and thereby minimizes the risk of transmission of germs, bacteria and the like. More specifically, in accordance with one aspect of the present invention the putty is a therapeutic putty that includes a borosiloxane compound which exhibits sufficient resistance and elasticity to render it suitable for hand exercise, and the borosiloxane compound includes an antimicrobial agent in a concentration sufficient to render the compound antimicrobial without adversely affecting the physical properties of the compound.

In accordance with another aspect of the present invention, the borosiloxane compound includes silicone oil, boric acid and one or more inert fillers, such as calcium carbonate or clays, or the like.

In accordance with another aspect of the present invention, the antimicrobial agent is a chlorophenyl ether, such as triclosan.

The antimicrobial therapeutic putty of the present invention advantageously remains substantially free of undesirable living contaminants, such as bacteria, fungi, viruses, and the like, that come into contact with the putty through normal use of the putty.

DETAILED DESCRIPTION OF THE INVENTION

The present invention now will be described more fully hereinafter with reference to preferred embodiments of the invention. This invention may, however, be embodied in many different forms and should not be construed as limited to the embodiments set forth herein; rather, these embodiments are provided so that this disclosure will be thorough and complete, and will fully convey the scope of the invention to those skilled in the art.

The putty of the present invention is preferably a kneadable putty such as a putty made from borosiloxane. Such putties have the ability to be manually kneaded and stretched, and can be provided in a variety of different resistances. Acceptable examples of borosiloxane putties are disclosed in U.S. Pat. No. 2,541,851 to Wright; U.S. Pat. No. 3,677,997 to Kaiser et al.; U.S. Pat. No. 5,319,021 to Christie; and U.S. Pat. No. 5,446,075 to Gibbon, the disclosures of which are incorporated herein by reference. In accordance with a specific exemplary embodiment of the present invention, the putty is made from polysiloxane-boron. More specifically, in accordance with the specific exemplary embodiment of the present invention the putty is made from one or more silicone oils, boric acid, and one or more inert fillers, such as calcium carbonate or clays, or the like.

The putty of the present invention includes an antimicrobial agent which is compatible with the putty material, and which is capable of destroying and/or inhibiting the growth of microorganisms such as bacteria, viruses, fungi and the like. Preferably, the antimicrobial agent is also selected to provide the putty with the antimicrobial physical characteristics while not adversely affecting the physical properties of the putty material (e.g., the antimicrobial agent preferably does not substantially affect the resistance, stretchability, useful life, or other qualities of the putty material).

The antimicrobial agent can be provided in any form such as liquid, dry, powder form, etc., and is preferably mixed into the putty during the manufacturing process. For example, the antimicrobial agent can be added and mixed along with the pigments or other putty additives such as by conventional equipment used to mix putty materials (e.g., by way of a large industrial strength mixer.) However, it is also within the scope of the invention for the antimicrobial agent to be added to the putty subsequent to the original manufacturing process. For example, the antimicrobial agent could be kneaded into the putty by the user subsequent to the initial manufacture of the putty. In other words, the antimicrobial agent could be provided separately and kneaded into the putty material prior to its use by a patient. Alternatively, putty could be provided having a greater concentration of antimicrobial agent than desired for the end product, and then kneaded in with conventional putty which does not have the antimicrobial agents, such that the end product includes an optimal amount of antimicrobial agent therein after the two putties are kneaded together by the user. In accordance with the specific exemplary embodiment of the present invention, the antimicrobial agent is added to the putty of the present invention as it is being manufactured, as described above.

Although the invention is not limited to a specific form of antimicrobial agent, the antimicrobial agent triclosan has been found to perform well in combination with borosiloxane putties such as those commercially available. Triclosan is provided by Ciba Specialty Chemicals Corporation of High Point, North Carolina and its distributors and is marketed under the trademark Irgasan®. Triclosan is a whitish fine crystalline powder, and it is also known as 2,4,4'-trichloro-2'-hydroxydiphenyl ether. When used in accordance with the present invention the triclosan is preferably at least approximately 99% pure. Triclosan is often used in antimicrobial soaps. Other types of antimicrobial agents can be used within the scope of the present invention. For example, triclosan is a chlorophenyl ether, and in accordance with other embodiments of the present invention other chlorophenyl ethers are used as the microbial agent incorporated into the putty. In addition, it is believed that other antimicrobial agents disclosed in U.S. Pat. Nos. 3,506,720 and 3,629,477, both of which are incorporated herein by reference, are suitable for being incorporated into the putty, in accordance with other embodiments of the present invention.

The antimicrobial agent is desirably provided in a concentration sufficient to render the putty antimicrobial without affecting the end use properties of the putty. For example and in accordance with the specific exemplary embodiment of the present invention, Irgasan®, which is preferably at least approximately 99% pure, is used as the antimicrobial agent and it is mixed into the putty so that the Irgasan® forms about 0.1% to 2% of the antimicrobial putty by weight, or more preferably about 0.25% to 1% of the antimicrobial putty by weight, and most preferably about 0.5% of the antimicrobial putty by weight. Other concentrations could be used within the scope of the invention, so long as they provide the desired antimicrobial effects without severely impacting the physical characteristics and functionality of the putty. However, it is believed that using greater amounts of the Irgasan® is not necessary.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A therapeutic putty for hand exercising, comprising:
   a polysiloxane-boron compound which exhibits sufficient resistance and elasticity to render it suitable for hand exercise, with said compound including an antimicrobial agent in a concentration sufficient to render the compound antimicrobial without adversely affecting the physical properties of the compound, said antimicrobial agent comprising chlorophenyl ether.

2. A therapeutic putty according to claim 1, wherein the antimicrobial agent comprises triclosan.

3. A therapeutic putty for hand exercising, comprising:
   a polysiloxane-boron compound which exhibits sufficient resistance and elasticity to render it suitable for hand exercise, with said compound including an antimicrobial agent in a concentration sufficient to render the compound antimicrobial without adversely affecting the physical properties of the compound,
   wherein the antimicrobial agent comprises chlorophenyl ether.

4. A therapeutic putty according to claim 3, wherein the antimicrobial agent comprises triclosan.

5. A therapeutic putty for hand exercising, comprising:
   a polysiloxane-boron compound which exhibits sufficient resistance and elasticity to render it suitable for hand exercise, with said compound including an antimicrobial agent in a concentration sufficient to render the compound antimicrobial without adversely affecting the physical properties of the compound,
   wherein the antimicrobial agent is 2,4,4'-trichloro-2'-hydroxydiphenyl ether.

* * * * *